United States Patent
Cicenas et al.

(10) Patent No.: US 7,740,597 B2
(45) Date of Patent: Jun. 22, 2010

(54) BIOPSY DEVICE WITH SAMPLE TUBE

(75) Inventors: Chris Cicenas, Columbus, OH (US); Luke Stonis, Columbus, OH (US); Beth McCombs, Sharon, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 236 days.

(21) Appl. No.: 10/732,843

(22) Filed: Dec. 10, 2003

(65) Prior Publication Data
US 2004/0153003 A1  Aug. 5, 2004

Related U.S. Application Data

(60) Provisional application No. 60/432,546, filed on Dec. 11, 2002.

(51) Int. Cl.
*A61B 10/00* (2006.01)

(52) U.S. Cl. ............... 600/566; 600/564; 600/565; 600/567; 600/568; 600/571

(58) Field of Classification Search ........... 600/564, 600/565, 566, 567, 568, 571
See application file for complete search history.

(56) References Cited

U.S. PATENT DOCUMENTS

| | | | |
|---|---|---|---|
| 5,183,052 A * | 2/1993 | Terwilliger | 600/566 |
| 5,195,533 A * | 3/1993 | Chin et al. | 600/567 |
| 5,526,822 A * | 6/1996 | Burbank et al. | 600/567 |
| 5,797,907 A | 8/1998 | Clement | |
| 5,944,673 A * | 8/1999 | Gregoire et al. | 600/564 |
| 6,019,733 A * | 2/2000 | Farascioni | 600/564 |
| 6,053,877 A * | 4/2000 | Banik et al. | 600/566 |
| 6,273,861 B1 * | 8/2001 | Bates et al. | 600/567 |
| 6,419,641 B1 | 7/2002 | Mark et al. | |
| 6,488,636 B2 * | 12/2002 | Bryan et al. | 600/566 |
| 6,517,498 B1 | 2/2003 | Burbank et al. | |
| 2004/0077972 A1 * | 4/2004 | Tsonton et al. | 600/564 |

OTHER PUBLICATIONS

EPO Search Report dated Apr. 5, 2004 for related European Patent Application No. PCT/US03/39364.

* cited by examiner

*Primary Examiner*—Max Hindenburg
*Assistant Examiner*—Helen Q. Nguyen

(57) ABSTRACT

A biopsy device is provided. The biopsy device includes cutter and a sample tube advancable through the hollow cutter to retrieve a tissue sample severed by the cutter. A vacuum source can be provided in communication with the sample tube. The sample tube can be releasably attached to the biopsy device.

19 Claims, 9 Drawing Sheets

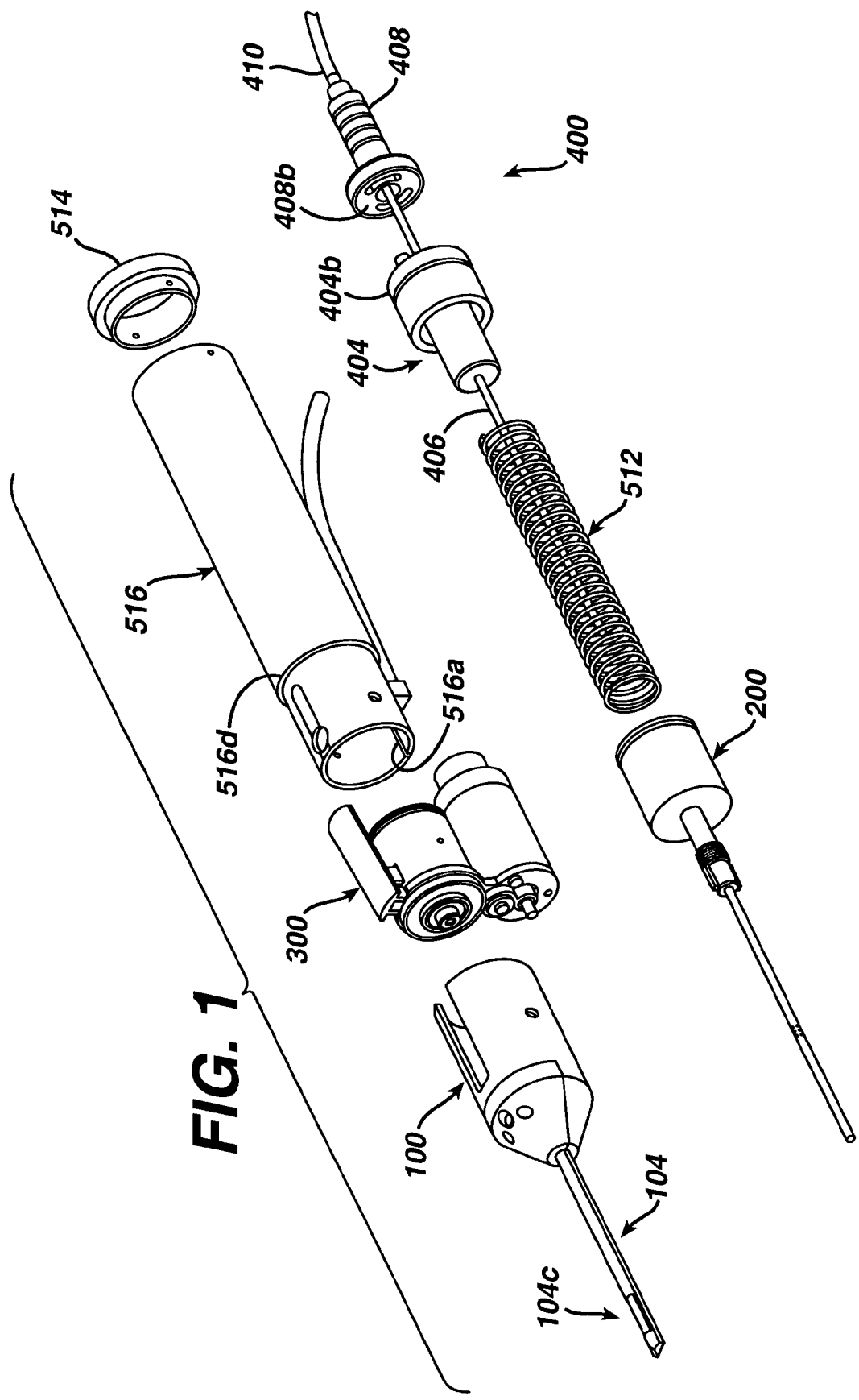

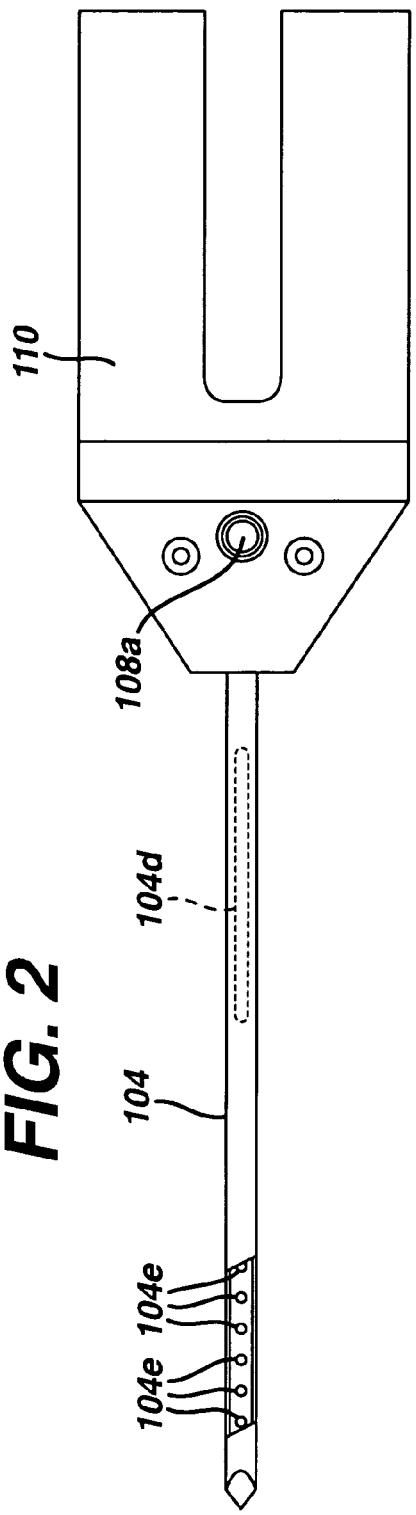
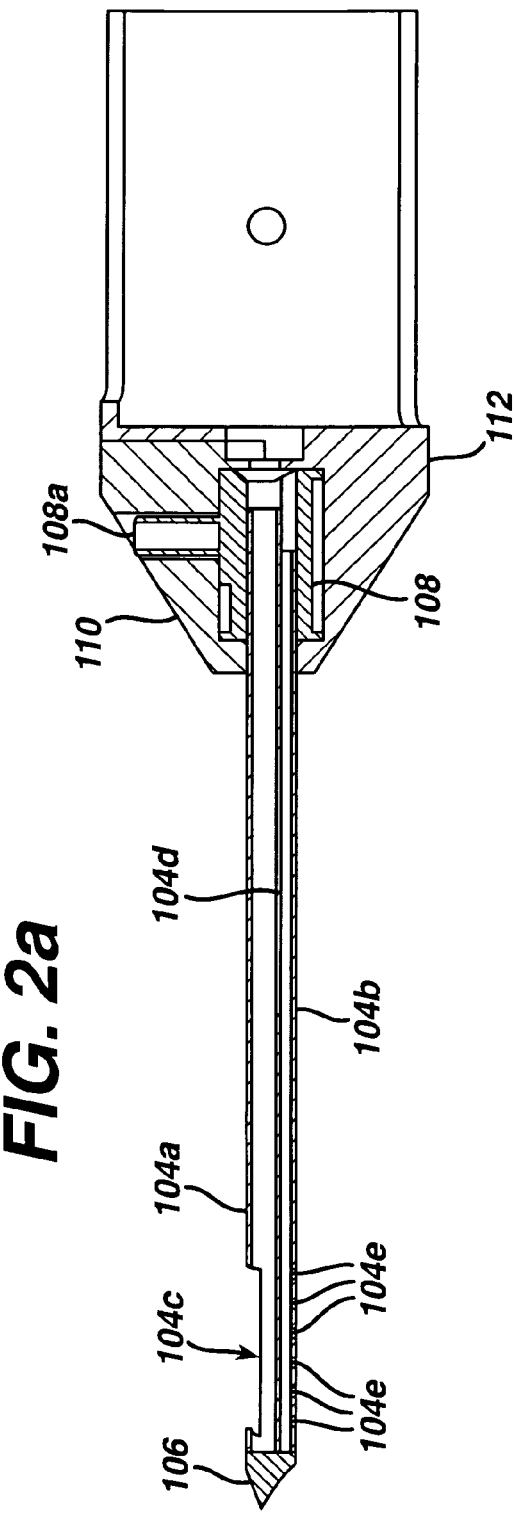

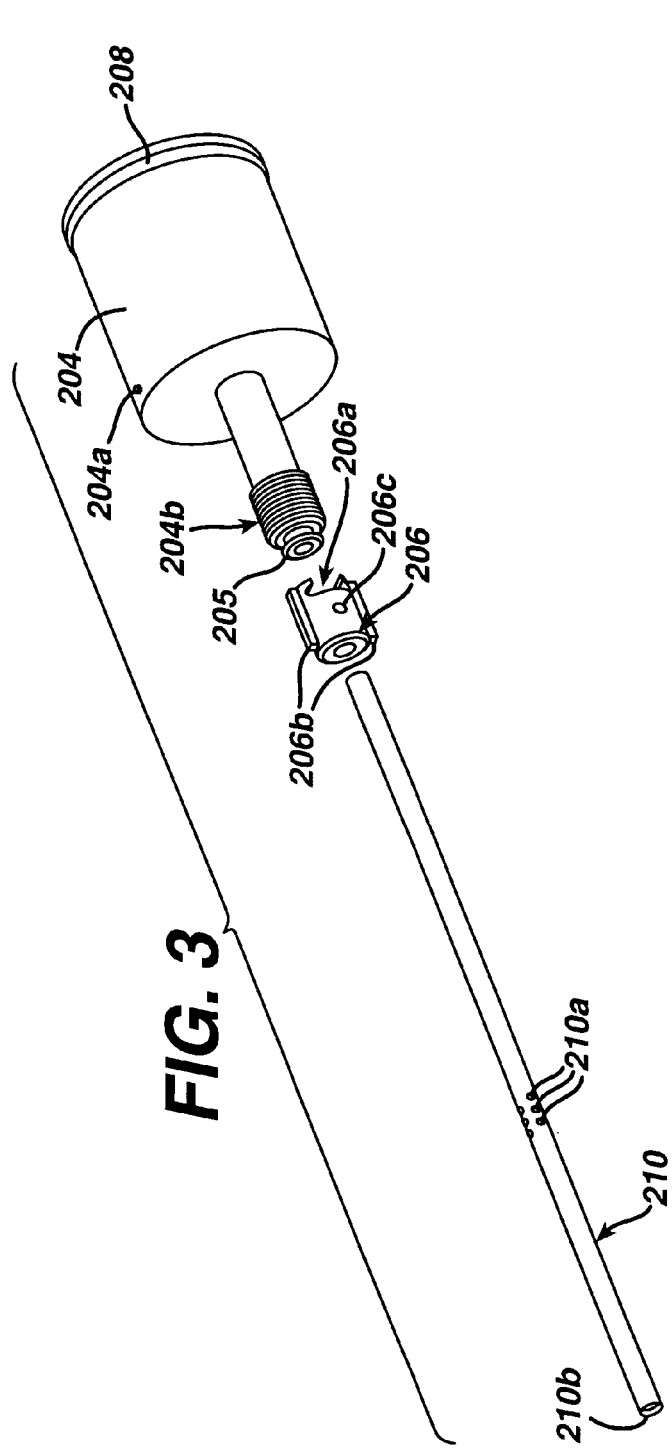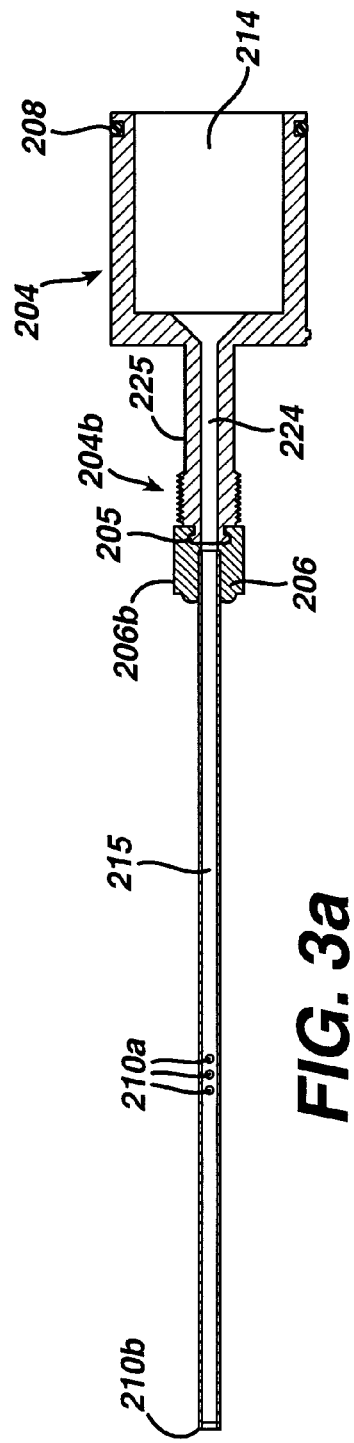

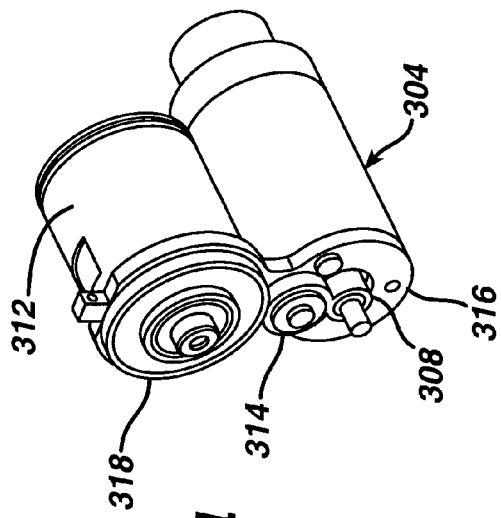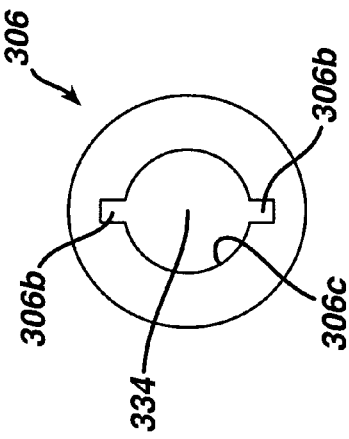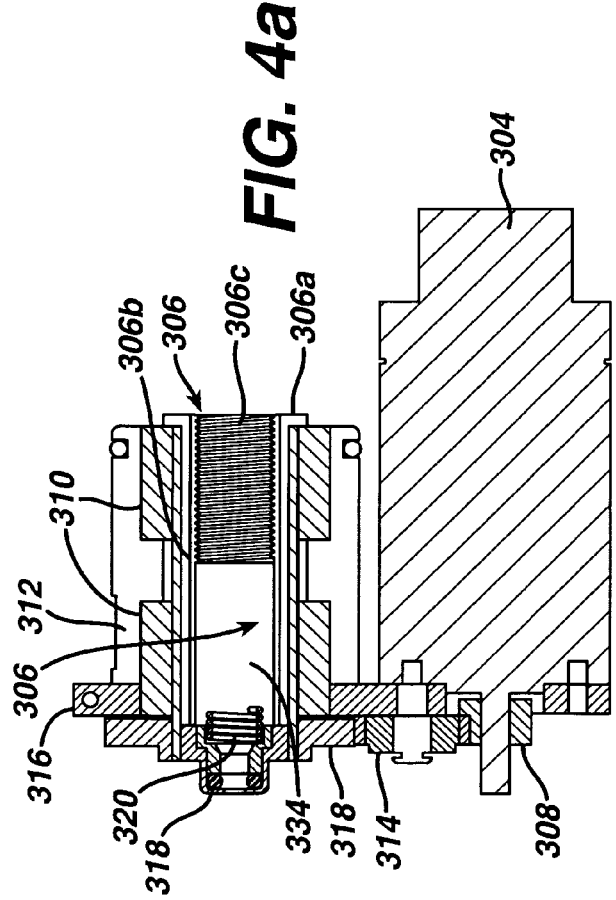

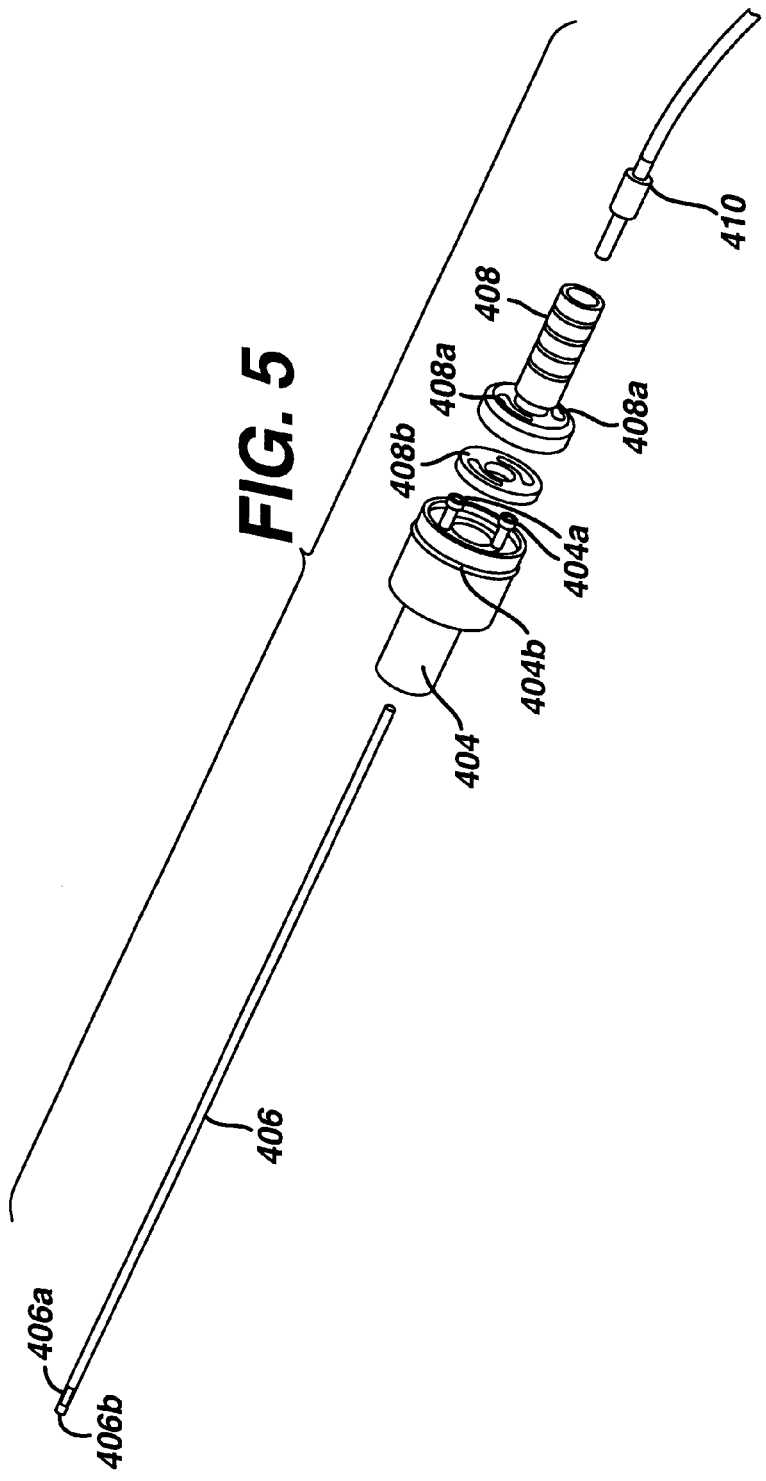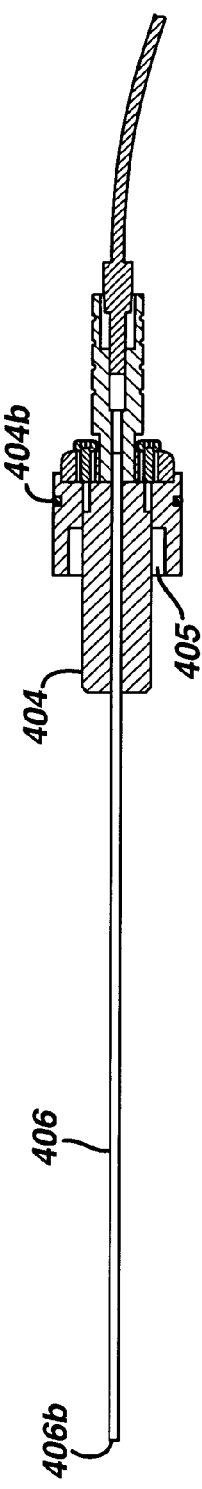

BIOPSY DEVICE WITH SAMPLE TUBE

The present invention claims priority to U.S. Provisional Patent Application 60/432,546 filed Dec. 11, 2002.

This patent application cross references and incorporates by reference the following copending patent applications: US Patent Application "Biopsy Device with Piston Advance" filed in the names of Cicenas et al. on even date herewith; and US Patent Application "Biopsy Instrument Having Internal Specimen Collection Mechanism" filed Sep. 30, 2003 in the names of Hibner et al. and having Ser. No. 10/676,944.

FIELD OF THE INVENTION

The present invention relates in general to biopsy devices and more particularly to methods and devices for handling samples obtained with a biopsy device.

BACKGROUND OF THE INVENTION

The diagnosis and treatment of patients with cancerous tumors is an ongoing area of investigation. Medical devices for obtaining tissue samples for subsequent sampling are known in the art. For instance, a biopsy instrument now marketed under the tradename MAMMOTOME is commercially available for use in obtaining breast biopsy samples.

Various imaging techniques including X-ray, MRI, CT, and ultrasound imaging may be used with biopsy devices for use in acquiring one or more tissue samples. It can be desirable to use an image guided, percutaneous biopsy instrument which is vacuum assisted, such as the MAMMOTOME device, to acquire multiple tissue samples without removing a biopsy needle between samples.

The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; US Patent Application publication 2003/0199753 published Oct. 23, 2003 to Hibner et al.

BRIEF SUMMARY OF THE INVENTION

The invention provides an apparatus and method useful for obtaining a biopsy sample. In one embodiment, the present invention provides a biopsy device comprising a hollow biopsy needle having a tissue receiving port; a hollow cutter advancable within the biopsy needle to sever tissue received within the tissue receiving port; and a sample tube advancable within the cutter. The sample tube can be releasably coupled to the biopsy device, so that the sample tube can be removed from the biopsy device, and tissue samples removed from the sample tube. A vacuum source can be provided in communication with the sample tube for providing axial vacuum through the cutter.

BRIEF DESCRIPTION OF THE FIGURES

FIG. 1 is a schematic illustration of subassemblies of a biopsy device according to one embodiment of the present invention.

FIG. 2 is top view illustration of the needle assembly in FIG. 1.

FIG. 2a is a cross-sectional illustration of the needle assembly illustrated in FIG. 1.

FIG. 3 is an enlarged schematic illustration of the main piston assembly shown in FIG. 1.

FIG. 3a is a cross-sectional schematic illustration of the main piston assembly.

FIG. 4 is a schematic illustration of the journal assembly shown in FIG. 1.

FIG. 4a is a schematic cross-sectional illustration of the journal assembly of FIG. 4.

FIG. 4b is a schematic illustration of the proximal end of the journal in FIG. 4a.

FIG. 5 is an enlarged schematic illustration of the floating piston assembly in FIG. 1.

FIG. 5a is a schematic cross-sectional illustration of the floating piston assembly in FIG. 5.

DETAILED DESCRIPTION

Figure 1A:
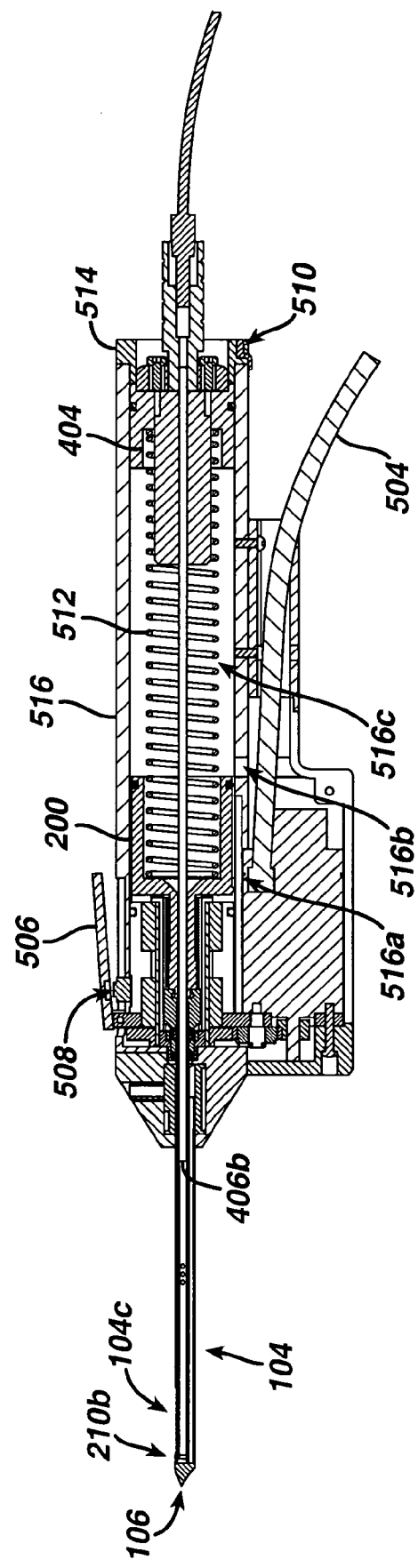
FIG. 1a is cross-sectional schematic illustration of the biopsy device assembled as shown in FIG. 1b.
Figure 1B:
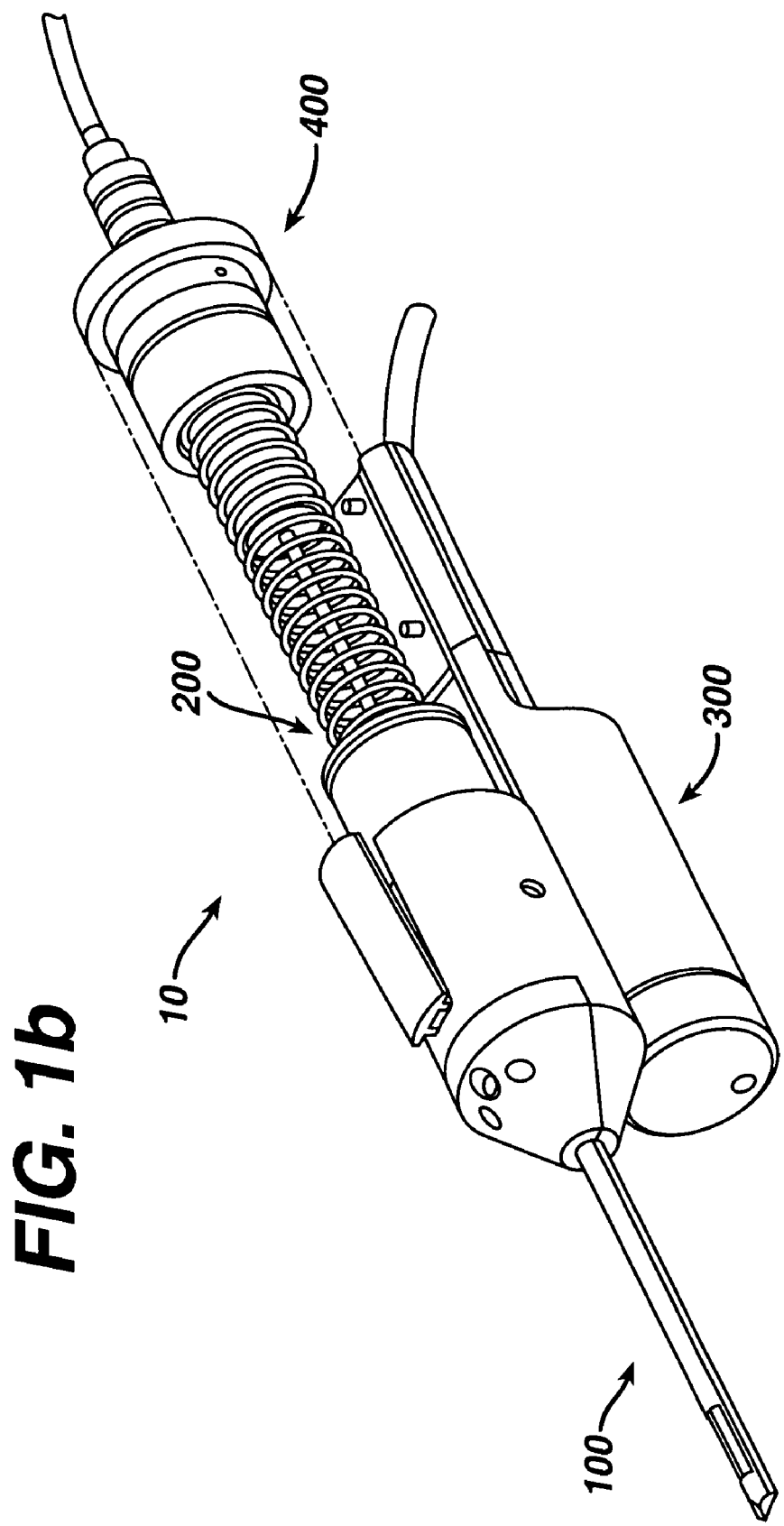
FIG. 1b is a perspective view of a biopsy device according to one embodiment of the present invention.

FIGS. 1, 1a, and 1b illustrate a biopsy device 10 according to one embodiment of the present invention. The biopsy device can comprise a needle assembly 100 (shown in more detail in FIGS. 2 and 2a), a main piston assembly 200 (shown in more detail in FIGS. 3 and 3a), a journal assembly 300 (shown in more detail in FIGS. 4 and 4a), a floating piston assembly 400 (shown in more detail in FIGS. 5 and 5a), and a tube 516, which can be a clear, thin walled tube.

Needle assembly 100 illustrated in FIGS. 2 and 2a can include an elongated hollow needle 104. Needle 104 comprises an upper cutter lumen 104a, a lower vacuum lumen 104b, a lateral tissue receiving port 104c communicating with the upper cutter lumen 104a, a plurality of interlumen vacuum holes 104e extending between the upper lumen 104a and the lower lumen 104b to communicate vacuum from the lower lumen to assist in drawing tissue into the port 104c. A sharpened distal tissue piercing tip 106 is disposed at the distal end of needle 104 and can fit within and close off the distal ends of the upper and lower lumens 104a and 104b. The needle 104 can also include an axially enlongated needle slot 104d positioned proximal of the port 104c and the interlumen vacuum holes 104e. The needle slot 104d can be used to provide communication between the upper lumen and the lower lumen of the needle 104 at a position proximal of the tissue receiving port 104c.

The needle 104 can be fixed, such as by adhesive or other suitable means, to needle support 108. Support 108 can be captured between the upper shell housing 110 and the lower shell housing 112. The upper and lower housings can be attached in any suitable manner, such as with screw fasteners, adhesive, or snap fit features.

A vacuum inlet port 108a can be provided in needle support 108. Vacuum inlet port 108a can be connected to an external source of vacuum (not shown). Vacuum can be provided to the lower lumen 104b via port 108a. Vacuum supplied to lumen 104b can be applied to lateral lateral tissue receiving port 104c via two paths: 1) via the lateral vacuum holes 104e between the upper lumen 104a and lower lumen 104b; and 2) via the distal needle slot 104d and the distal portion of the upper lumen 104a.

The main piston assembly illustrated in FIGS. 3 and 3a can comprise a main piston 204, an o-ring seal 208 disposed in a groove in the outer surface of piston 204 to provide sealing between piston 204 and the inside surface of tube 516, a cutter clutch 206, and a cutter 210. Piston 204 can include a cavity 214 opening at the proximal face of the piston 204, a distally extending shaft portion 225, and a central bore 224 extending through the shaft portion 225.

The piston 204 can include a threaded portion 204b on the shaft portion 225. At the distal end of the threaded portion 204b, a circumferentially extending lip 205 can be provided. Lip 205 can engage with a complimentary slot feature 206a disposed in the proximal end of cutter clutch 206, such that cutter clutch 206 and piston 204 are coupled together for axial movement, but such that cutter clutch 206 can rotate relative piston 204 about a longitudinal axis extending through the center of the piston 204 and parallel to cutter 210.

Cutter 210 can be attached to the cutter clutch 206 by any suitable means, such as by a set screw 206c. Cutter clutch has a central bore therethrough, which is aligned with the central bore 224 of piston 204 when the piston 204 and cutter clutch 206 are coupled together by lip 205 and slot feature 206a. Cutter 210 can be in the form of a hollow tube with a sharpened distal end 210b. Hollow cutter 210 has a central lumen 215 extending therethrough which is aligned with the central bore of the cutter clutch and the central bore 224 of piston 204. Cutter 210 can further include a plurality of radial holes 210a which are positioned intermediate the cutter clutch 206 and the distal sharpened end 210b. The radial holes extend through the wall of the hollow cutter 210 and communicate with central lumen 215.

Cutter clutch 206 can have a generally cylindrical shaped body with surface features extending therefrom, such as engagement wings 206b. In FIG. 3 there are two wings 206b shown spaced at approximately 180 degree intervals around the circumference of the cutter clutch 206. Wings 206b can serve to releasably key or otherwise releasably engage clutch 206 with another member for rotation therewith, as described more fully below.

The journal assembly 300 illustrated in FIGS. 4, 4a, and 4b can comprise a journal housing 312, a motor 304 for driving rotation of a journal 306 mounted within housing 312 through a gear train. The gear train can comprise a pinion gear 308, and intermediate gear 314, and a driven gear 318. The pinion gear can be mounted to the drive shaft of motor 304, and the motor 304 and intermediate gear 314 can be supported by a bracket 316 which can be attached to a distal face of the journal housing 312.

The driven gear 318 can be mounted to journal 306. Journal 306 is supported for rotation about a longitudinal axis by bearings 310. Journal 306 includes a longitudinally extending central bore 334 therethrough. Journal 306 has a threaded feature 306c comprising an internally threaded portion extending from proximal end of the central bore 334. Journal 306 can also include a channel feature 306b for use in engaging the wings 206b of cutter clutch 206. Channel feature 306b can comprise two longitudinally extending slots spaced about 180 degrees apart around the inner surface of bore 334, as shown in FIG. 4b. The slots of channel feature 306b can have a depth which is greater than the depth of the threads of threaded feature 306c. The slots of channel feature 306b can extend the length of journal 306.

The driven gear can bear against a thrust washer, which can bear against the distal end of the journal housing to constrain journal 306 axially. The proximal end of the journal 306 can be constrained by a journal flange 306a, which can bear against a thrust washer. The journal 306 can be constrained radially by, and be rotatably within, bearings 310 disposed in the journal housing (312).

The floating piston assembly shown in FIGS. 5 and 5a can comprise a floating piston 404 having a central bore therethrough, o-ring 404b, hollow sample tube 406, sample tube receiver 408, magnet 408b, and rear axial vacuum line 410. The piston 404 can have a spring seat 405 for receiving the end of a spring. The sample tube 406 can have a retaining notch 406a in the wall of the tube positioned near the open distal end 406b of tube 406. The sample tube 406 can extend through the central bore of the piston 404 and be press fit into the proximal end of the sample tube receiver 408 such that sample tube 406 can be easily inserted and removed one or more times. The receiver 408 has a passageway therethrough for communicating vacuum from vacuum line 410 to sample tube 406. The receiver 408 can be configured to releasably lock onto the floating piston 404 by any suitable mechanism, such as a twist lock mechanism comprising retaining bosses 404a on the floating piston 404 and corresponding receiver slots 408a on the straw receiver 408. The twist lock mechanism allows the receiver 408 and sample tube 406 to be releasably coupled to the biopsy device, such that the sample tube 406 can be inserted into the device, and then withdrawn from the device once one or more samples have been received in sample tube 406. A circular magnet 408b can be disposed in a recess in the distal face of the straw receiver 408. An o-ring 404b can be provided in a groove on the outer surface of floating piston 404 to provide sealing with the inner surface of tube 516 as piston 404 translates within tube 516. The rear axial vacuum line 410 can be press fit into the rear of receiver 408 and enables vacuum to be drawn through the center of the sample tube 406 as the device is operated.

A portion of the journal assembly 300 can be sized and shaped to fit inside the distal end of clear, thin-wall tube 516. Tube 516 can be made from a lightweight transparent material, such as clear plastic or polymeric material, to permit viewing of the device during operation. The proximal end of the needle assembly 100 can then be positioned over a reduced diameter distal end portion of the clear, thin-wall tube 516 that extends distally from a lip feature 516d of the tube 516. The needle assembly 100 and journal assembly 300 can be attached to the thin wall tube 516 by any suitable means, such as by a plurality of screws.

The main piston assembly 200 is supported for translation within the clear, thin-walled tube 516 and is positioned proximally of the journal assembly 300. The main piston assembly 200 is keyed to the tube 516 by a piston guide tab 204a (FIG. 3) on the main piston 204 and a channel feature 516a (FIG. 1a) located on the tube 516. Tab 204a rides in channel 516a to allow main piston assembly 200 to translate axially inside the tube 516 while preventing the main piston 204 from rotating relative to the tube 516. An o-ring 208 seated in a groove on the outer surface of main piston 204 provides an air seal between the main piston 204 and inner surface of tube 516.

The floating piston assembly 400 can be disposed inside the clear, thin-wall tube 516 and is positioned between the main piston assembly 200 and the end cap 514. The end cap 514 can be fastened to the proximal end of the tube 516 by any suitable means including by fasteners, snap fit, or threaded engagement. O-ring 404b seated in a groove on the outside surface of floating piston 404 provides an air seal between the floating piston 404 and the inside surface of tube 516.

A return spring 512 is captured between the main piston assembly 200 and floating piston assembly 400. The distal end of the return spring 512 can be seated in cavity 214 of main piston 204, and the proximal end of the return spring 512 can be seated within annular seat 405 of floating piston 404. The return spring 512 provides constant forward (distal) biasing force against the main piston assembly 200. Therefore, when the main piston assembly 200 is in its rearward (proximal) most position, the distal end of threaded feature 204b is maintained in contact with the proximal end of a journal threaded feature 306c due to the spring force provided by spring 512. The biasing spring force provided by spring 512 also maintains two engagement wings 206b on the cutter clutch 206 in engagement with channel slot features 306b of the journal 306. Engagement of the wings 206b with slot features 306b causes cutter clutch 206 (and so cutter 210) to rotate when journal 306 is rotated by motor 304. In the embodiment shown, piston 204 does not rotate.

Engagement of the journal's internal threads 306c with the main piston's external threads 204b causes cutter clutch 206 (and so cutter 210) to advance in lead screw fashion at a speed based on the number of threads per inch and the speed of rotation of the journal. With this mechanism, translation and rotation of cutter 210 is provided by rotation of journal 306 driven by a single motor 304.

The motor 304 can be operated to rotate clockwise, advancing and rotating the cutter 210 so the distal end of the cutter 210 advances in the upper lumen of needle 104 past the tissue receiving port 104 and cuts a tissue sample through the lateral port 104c in the needle assembly 100. Once the cutter 210 has fully translated past the needle lateral port 104c, the main pistons threaded feature 204b "rides" off the distal end of the journal's threaded feature 306c, thereby preventing further translation forward. However, the motor 304 can be operated to continue to rotate a predetermined number of rotations, rotating the journal's channel feature 306b and therefore the cutter 210 for additional revolutions to guarantee the tissue sample has been completely separated from the main body of tissue being sampled.

Once the main piston assembly 200 has translated to its forward most (distal most) position, the clutch return spring 320 is compressed, pushing against the cutter clutch 206, to keep the proximal end of the main piston's threads (204b) and the distal end of the journal's threads (306c) in constant contact with each other. The spring 320 provides a biasing force to ensure the threads will engage and the main piston assembly 200 will retract when the motor 304 is operated in reverse.

The end cap 514 can include a Hall effect sensor. The Hall effect sensor in conjunction with magnet 408b associated with the receiver 408, can provide a signal when the sample tube is removed from the device, which signal can be used to turn the external vacuum through tube 406 on and off, or otherwise control the external vacuum source.

The hollow needle 104 can be positioned into a tissue mass, such as with the aid of any suitable imaging device. To begin operation of the biopsy device the assembly of the sample tube 406, magnet 408b, receiver 408, and vacuum line 410 can be inserted into and releasably coupled to the floating piston 404 using the bosses 404a. Upon insertion of the receiver 408 through the end cap 514 the external vacuum source can be turned on via the Hall effect sensor 510 and the magnet 408b that is supported inside the receiver 408.

To activate the biopsy device, the physician can depress 506. Lever 506 activates an electromechanical momentary contact switch 508 to begin rotation of motor 304 and journal 306. Rotation of journal 306 draws main piston assembly 200 forward (distally).

Referring to FIG. 1a, after the cutter 210 has advanced forward completely to sever a tissue sample, vacuum can be applied from an external source through a vacuum tube 504 and port 516b in tube 516 that communicates vacuum into a chamber 516c on the distal side of the floating piston 404. Vacuum in chamber 516c pulls the floating piston 404 forward, so that the distal end 406b of the sample tube 406 advances inside the cutter 210. With the cutter 210 fully advanced, the distal end of the sample tube 406 advances to the distal end of the needle lateral port 104c, thereby encapsulating the tissue sample with slight radial compression applied to the tissue sample. Once the tissue sample is encapsulated, the vacuum to line 504 can be turned off and atmospheric pressure can be provided to the distal face of the floating piston 404, so that the return spring 512 pushes the floating piston assembly 400 back to the retracted position shown in FIG. 1a.

The physician may then press the button 506, which activates the electromechanical switch 508 a second time, causing the motor 304 to rotate in the opposite direction, thereby retracting the cutter 210. The clutch return spring 320 presses the piston assembly 200 back onto the journal's threaded feature 306c, so that engagement is ensured. The journal 306 spins in the opposite direction, causing the piston assembly 200 to retract so the distal end 210b of cutter 210 is positioned just proximal of the proximal end of the lateral needle port 104c. Accordingly, the full travel of the cutter 210 can be from just proximal of the port 104c to just distal of port 104c.

To take a second tissue sample, the user presses lever 506 to activate the electromechanical switch 508 and provide motor 304 rotation in the forward direction to rotate and translate the cutter through the needle's lateral port 104c, so as to sever tissue drawn into port 104c by vacuum provided via lumen 104b. After the cutter 210 has completely separated a second tissue specimen, vacuum pressure can again be applied via port 516b to the distal face of the floating piston 404, so that piston 404 and sample tube 406 are advanced, with the distal end of tube 406 advanced to the distal end of the needle lateral port 104c. The second tissue sample is encapsulated by the sample tube 406. As the second tissue sample enters the sample tube 406, the first tissue sample is displaced rearward into the sample tube 406. In this manner, multiple samples can be stacked within a sample tube 406 until the sample tube 406 contains a plurality of tissue specimens.

Figure 7:
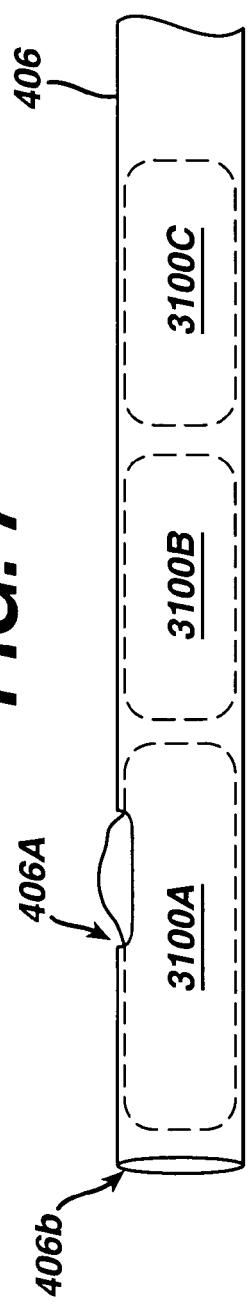
FIG. 7 is a schematic illustration of tissue sample stacking in a sample tube.

FIG. 7 illustrates stacking of successive tissue samples 3100A-3100C in sample tube 406. The sample tube inner diameter can be sized so that the cut tissue samples are slightly compressed within the sample tube.

When the tube 406 contains the desired number of severed tissue specimens, the user may release the sample tube 406 by rotating the receiver 408 slightly to expose the wider portion of the slots 408a to allow the slots 408a to clear the retaining bosses 404a. When the receiver 408 is removed with the sample tube 406 attached, magnet 408b within the straw receiver 408 passes a Hall effect sensor 510 in end cap 514, which can provide a signal for use in turning off the external vacuum source communicating through vacuum line 410.

In one embodiment, a tissue retention feature in the wall of tube 406, such as rectangular notch 406a, is provided near the distal end of the sample tube 406. Notch 406a can allow the most recently acquired sample near the distal end of the sample tube 406 to expand or bulge slightly out of opening provided by notch 406a. The notch thereby aids in retaining the most recently obtained sample within sample tube 406.

Additionally, vacuum applied to samples from vacuum line 410 through the sample tube 406 can apply a force to the distal end of the tissue sample, which can assist in balancing any axial vacuum force that may be applied to the tissue samples by vacuum provided through interlumen vacuum holes 104e. Other suitable tissue retention features, such as one or more indentations in the tube wall, could be employed to assist in retaining tissue samples.

To remove tissue samples from the sample tube 406 once the tube 406 has been removed from tube 516, the user may remove tube 406 from receiver 408. The user may then cover the rectangular notch 406a with a finger, compressing the sample back into the sample tube 406, while pushing a rod through the sample tube 406 to push the samples out of the tube. Once the sample has traveled past the rectangular notch 406a, the finger can be removed and the sample(s) can be pushed out of the tube. Alternatively, a saline filled syringe may be attached to one end of the sample tube 406, and saline may be used to push the samples out of the tube 406.

Figure 6:
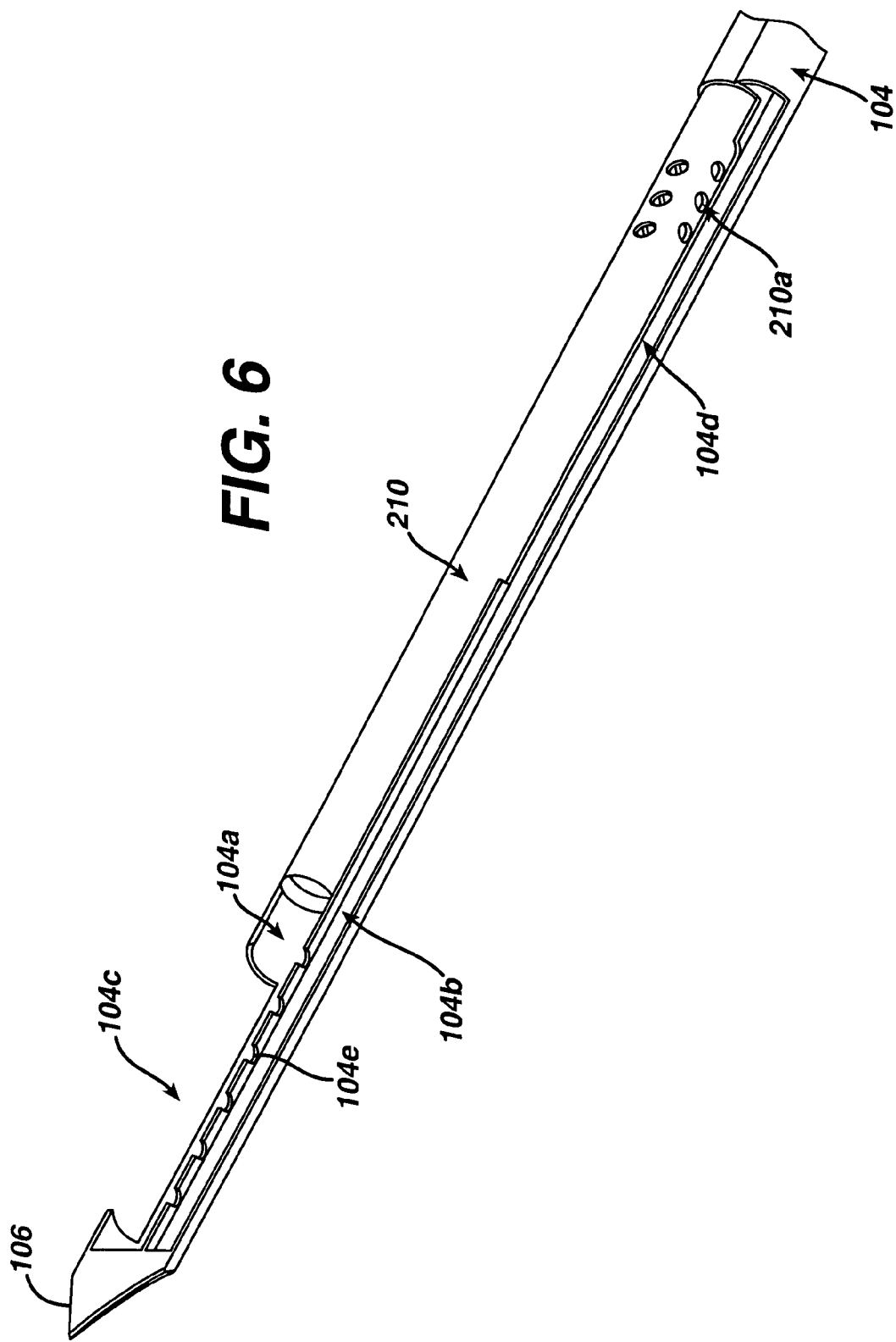
FIG. 6 is a schematic cut away illustration of a portion of the cutter assembly with the cutter positioned just proximal of the lateral tissue receiving port of the needle.

Referring to FIG. 6, needle 104 can include needle slot 104d between the upper cutter lumen 104a and lower vacuum lumen 104b. When vacuum is applied from the external vacuum source through the inlet port 108a (FIG. 2) to the needle lower lumen 104b, vacuum is applied both through the proximal needle slit 104d and the lateral vacuum holes 104e. Staggered radial holes 210a (these holes can be circular, rectangular, or any other suitable shape) in the cutter 210 align with and communicate with the distal needle slot 104d as the distal end of the cutter 210 rotates and translates through the needle lateral port 104c. Therefore, vacuum is communicated to the internal lumen of the cutter 210 from the lower lumen 104b via the distal slit 104d and the staggered radial cutter holes 210a. In this way, during sampling, and even with tissue samples in tube 406, vacuum is applied both laterally to the tissue through interlumen vacuum holes 104e as well as axially through cutter 210 via the distal needle slot 104d and cutter holes 210a to assist in maximizing tissue sample size. Vacuum provided by vacuum line 410 through sample tube 406 and then through cutter 210 can provide axial vacuum force for assisting in obtaining suitable samples through port 104c when there are no previously severed samples in sample tube 406. Slot 104d and cutter holes 210a can be employed to provide axial vacuum at the port 104c even if samples are present in the sample tube 406.

Figure 8:
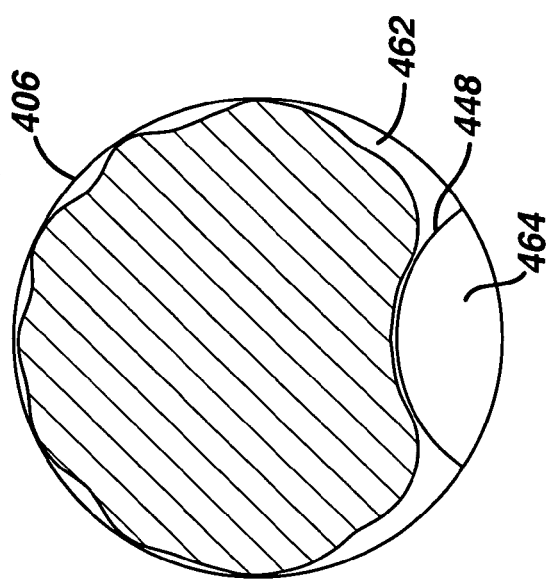
FIG. 8 is a schematic cross-section illustration of a sample tube having an internal vacuum lumen.

FIG. 8 shows an alternative embodiment of sample tube 406 having an internal wall 448 to provide a first sample lumen 462 and a second vacuum lumen 464. Each of lumen 462 and 464 can be in communication with a source of vacuum such as that provided via vacuum line 410. Vacuum lumen 464 can employed to provide axial vacuum at port 104c when samples are present in lumen 462 of sample tube 406.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

What is claimed:

1. A biopsy device comprising:
   a hollow biopsy needle having a tissue receiving port;
   a hollow cutter advanceable within the biopsy needle to sever tissue received within the tissue receiving port, wherein the cutter has a sidewall surrounding an interior, wherein the cutter has a plurality of holes spaced from the distal end of the cutter, wherein the plurality of holes are formed transversely through the sidewall of the cutter for providing fluid communication from a region exterior to the sidewall of the cutter to the interior of the cutter, and wherein the holes are positioned for providing vacuum axially through the cutter when multiple tissue samples are disposed within a sample tube within the cutter; and
   the sample tube advanceable within the hollow cutter, the sample tube having an open distal end sized for receiving a tissue sample severed by the hollow cutter, the sample tube being releasably supported on the biopsy device such that the sample tube and at least one tissue sample stored therein may be removed from the biopsy device without disassembling the biopsy device, wherein the sample tube comprises a vacuum lumen and a sample lumen, wherein the vacuum lumen extends along side of at least a portion of the sample lumen,
   wherein the hollow cutter is operable to be advanced to a distal most position within the hollow biopsy needle to sever the tissue sample, and
   wherein the sample tube is operable to be advanced to the distal most position within the hollow cutter to receive the tissue sample after the tissue sample has been completely severed.

2. The biopsy device of claim 1 wherein the sample tube is adapted to store multiple samples in an end to end configuration.

3. The biopsy device of claim 1 comprising a vacuum source in communication with the sample tube.

4. The biopsy device of claim 1 wherein the sample tube is advanced by fluid pressure.

5. The biopsy device of claim 1 wherein the sample tube is advanced pneumatically.

6. The biopsy device of claim 1 comprising a piston operatively associated with the sample tube.

7. The biopsy device of claim 1 comprising an apparatus for advancing and retracting the cutter within the biopsy needle.

8. The biopsy device of claim 7 comprising an apparatus for advancing and retracting the sample tube within the cutter.

9. The device of claim 1 wherein the hollow needle comprises a lateral tissue receiving port spaced from the distal end of the needle.

10. The device of claim 1 wherein the sample tube comprises a tube wall feature for retaining tissue samples.

11. The device of claim 10 wherein the tube wall feature comprises a notch disposed adjacent the distal end of the sample tube.

12. The biopsy device of claim 1 comprising a rotating journal for rotating and advancing the cutter.

13. A biopsy device comprising:
   a hollow biopsy needle having a closed distal end and a lateral tissue receiving port spaced proximally of the closed distal end;
   a hollow cutter having an open distal end, a lumen extending proximally from the open distal end, and a plurality of holes extending through a wall of the cutter, the cutter advanceable to a distal most position within the biopsy needle to sever tissue received within the tissue receiving port;
   a sample tube having an open distal end defining a distal opening, the sample tube being releasably supported on the biopsy device, and the sample tube advanceable within the cutter;

a drive mechanism for advancing and rotating the cutter within the biopsy needle; and a sample tube advancement assembly, wherein the sample tube advancement assembly is operable to advance the sample tube to the distal most position within the cutter to store a tissue sample within the sample tube after the cutter has been advanced within the needle to the distal most position to sever the tissue sample, wherein the sample tube comprises a vacuum lumen and a sample lumen, and wherein the vacuum lumen extends along side of at least a portion of the sample lumen.

14. A method of obtaining a tissue sample comprising the steps of:

drawing tissue into a side tissue receiving port of a hollow biopsy needle;

advancing a hollow cutter in the needle to sever a tissue sample and to encapsulate the severed tissue sample within the cutter upon reaching a distal most position in the hollow biopsy needle, wherein the cutter closes the tissue receiving port when the cutter is at the distal most position;

advancing a hollow sample tube to the distal most position in the cutter to position the tissue sample in the sample tube, wherein the hollow sample tube has an open distal end, wherein the open distal end comprises a distally facing opening defined by the distal most perimeter of the open distal end, wherein the tissue sample is axially received in the hollow sample tube through the opening at the open distal end of the hollow sample tube during the act of advancing the hollow sample tube, wherein at least a portion of the act of advancing the hollow sample tube is performed after the cutter has reached the distal most position and after the cutter has encapsulated the severed tissue sample; and wherein the sample tube comprises a vacuum lumen and a sample lumen, wherein the vacuum lumen extends along side of at least a portion of the sample lumen;

and wherein the method comprises providing vacuum to the sample tube vacuum lumen.

15. The method of claim 14 comprising stacking multiple samples within the sample tube in an end to end configuration along a length of the tube.

16. The method of claim 14 comprising providing axial vacuum in the cutter with at least one sample disposed in the sample tube.

17. The biopsy device of claim 13, wherein the sample tube advancement assembly comprises a vacuum chamber and a floating piston.

18. The method of claim 14, wherein the sample tube remains stationary during the act of advancing the hollow cutter.

19. A needle assembly comprising a hollow biopsy needle having a closed distal end having a tissue piercing tip and a side tissue receiving port spaced proximally of the closed distal end, a cutter lumen, and a vacuum lumen, and wherein the needle comprises an axially extending slot positioned proximal of the side tissue receiving port, the axially extending slot communicating between the cutter lumen and the vacuum lumen;

a hollow cutter advanceable within the biopsy needle to sever tissue received within the tissue receiving port, wherein the cutter has a sidewall surrounding an interior, wherein the cutter has an open distal end and plurality of holes spaced from the distal end of the cutter, wherein the plurality of holes are formed transversely through the sidewall of the cutter for providing fluid communication from a region exterior to the sidewall of the cutter to the interior of the cutter;

a sample tube advanceable within the hollow cutter, the sample tube having an open distal end sized for receiving a tissue sample severed by the hollow cutter the sample tube being releasably supported on the biopsy device such that the sample tube and at least one tissue sample stored therein may be removed from the biopsy device without disassembling the biopsy device; and a vacuum source operable to communicate vacuum through the sample tube, wherein the hollow cutter is operable to be advanced to a distal most position within the hollow biopsy needle to sever the tissue sample, and wherein the sample tube is operable to be advanced to the distal most position within the hollow cutter to receive the tissue sample after the tissue sample has been completely severed.

* * * * *